United States Patent [19]

Leeds

[11] Patent Number: 5,571,808
[45] Date of Patent: Nov. 5, 1996

[54] METHOD FOR TREATING SMOKING-RELATED BONE LOSS

[75] Inventor: James P. Leeds, Noblesville, Ind.

[73] Assignee: Eli Lilly and Company, Indianapolis, Ind.

[21] Appl. No.: 381,036

[22] Filed: Jan. 31, 1995

[51] Int. Cl.$^6$ .......... A61K 31/55; A61K 31/445; A61K 31/40; A61K 31/185
[52] U.S. Cl. .......... 514/212; 514/315; 514/317; 514/319; 514/324; 514/422; 514/578; 514/333
[58] Field of Search .......... 514/315, 578, 514/333, 422, 317, 319, 324

[56] References Cited

U.S. PATENT DOCUMENTS 5,393,763  2/1995  Black et al. .......... 514/333

FOREIGN PATENT DOCUMENTS 0584952  3/1994  European Pat. Off. .

OTHER PUBLICATIONS

Jordan et al., "Effects of anti-estrogens on bone in castrated and intact female rats," *Breast Cancer Research and Treatment*, 10, 31–35 (1987).

Slemenda, "Cigarettes and the Skeleton," *N. Engl. J. Med.*, 330, 430–431 (1994).

Hopper and Seeman, "The Bone Density of Female Twins Discordant for Tobacco Use," *N. Engl. J. Med.*, 330, 387–392 (1994).

Jensen et al., "Cigarette Smoking, Serum Estrogens, and Bone Loss During Hormone–Replacement Therapy Early After Menopause," *N. Engl., J. Med.*, 313, 973–975 (1985).

Kiel et al., "Smoking Eliminates the Protective Effect of Oral Estrogens on the Risk for Hip Fracture Among Women," *Ann. Intern. Med.*, 116, 716–721 (1992).

*Primary Examiner*—Theodore J. Criares
*Attorney, Agent, or Firm*—James P. Leeds; David E. Boone

[57] ABSTRACT

A method for treating smoking-related bone loss comprising administering to a human in need thereof a pharmaceutically-effective amount of a compound having the formula

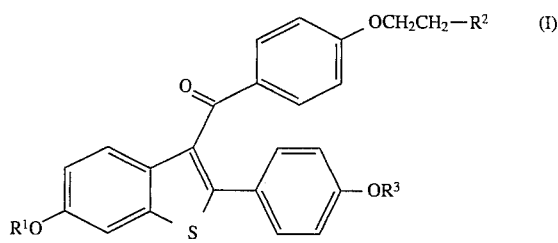

wherein $R^1$ and $R^3$ are independently hydrogen, $C_1$-$C_4$ alkyl, —CO—($C_1$-$C_6$ alkyl), or —CH$_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

6 Claims, No Drawings

METHOD FOR TREATING SMOKING-RELATED BONE LOSS

BACKGROUND OF THE INVENTION

This invention relates to the discovery that a group of 2-aryl-3-aroylbenzo[b]thiophenes is useful in the treatment of smoking-related bone loss.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications. Unchecked, bone loss can lead to osteoporosis, a major debilitating disease whose prominent feature is the loss of bone mass (decreased density and increased porosity) without a reduction in bone volume, producing porosity and fragility.

Recent studies have suggested that smoking is a risk factor for bone fractures, especially of vertebral, forearm, and hip fractures. In one study, bone density of women who smoked, or who smoked more heavily, was significantly lower than that of their twin sisters. See Hopper and Seeman, *N. Engl. J. Med.*, 330(6), 387–392 (1994). A decrease in bone density means an increased risk of osteoporotic fractures. In a second study, bone loss was accelerated in middle-aged men who were smokers. See Slemenda et al., *Ann. Intern. Med.*, 117, 286–291 (1992). These studies provide compelling evidence of an association between smoking and reduced bone density in both men and women.

Estrogen, either alone or combined with progestin, is currently recommended for preventing bone loss in postmenopausal women. Although estrogens have beneficial effects on bone, long-term estrogen therapy has been implicated in a variety of disorders, including an increased risk of uterine and breast cancer. Furthermore, the protective effects of estrogen therapy are eliminated for women smokers. See Kiel et al., *Ann. Intern. Med.*, 116(9), 716–721 (1992). This lack of protection is due to smoking-related increases in the sex-hormone binding globulin and hepatic metabolism of estrogens. See Slemenda, *N. Engl. J. Med.*, 330(6), 430–431 (1994) and Jensen et al., *N. Engl. J. Med.*, 313(6), 973–975 (1985). Therefore, there currently exists a need for treatment of bone loss in both men and women who smoke.

The present invention provides methods for treating smoking-related bone loss, thus serving as an effective and acceptable treatment for smoking-related osteoporosis.

The 2-aryl-3-aroylbenzo[b]thiophene compounds that are used in the methods of this invention were first developed by Jones and Suarez as anti-fertility agents. See U.S. Pat. No. 4,133,814 (issued Jan. 9, 1979). These compounds are generally useful in suppressing the growth of mammary tumors.

Jones later found that a group of compounds are useful for antiestrogen and antiandrogen therapy, especially in the treatment of mammary and prostatic tumors. See U.S. Pat. No. 4,418,068 (issued Nov. 29, 1983). One of these compounds, 6-hydroxy-2-(4-hydroxyphenyl)-3-[4-(2-piperidinoethoxy)benzoyl]benzo[b]thiophene was clinically studied for the treatment of breast cancer. This compound is called raloxifene, formerly keoxifene.

SUMMARY OF THE INVENTION

This invention provides methods for treating smoking-related bone loss, comprising administering to a human in need thereof an effective amount of a compound of the formula

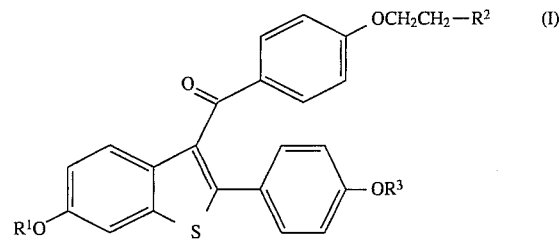

wherein

R$^1$ and R$^3$ are independently hydrogen, C$_1$–C$_4$ alkyl, —CO—(C$_1$–C$_6$ alkyl), —CH$_2$Ar, or —CO—Ar, wherein Ar is phenyl or substituted phenyl;

R$^2$ is selected from the group consisting of pyrrolidino, hexamethyleneimino, and piperidino; or a pharmaceutically-acceptable salt thereof. The present invention also provides the use of the formula I compounds, or pharmaceutically-acceptable salts thereof, for the manufacture of a medicament for the treatment of smoking-related bone loss.

DETAILED DESCRIPTION OF THE INVENTION

The present invention concerns the discovery that a select group of 2-aryl-3-aroylbenzo[b]thiophenes (benzo[b]-thiophenes), the compounds of formula I, are useful for treating smoking-related bone loss. The therapeutic treatments provided by this invention are practiced by administering to a human in need thereof a pharmaceutically-effective amount of a compound of formula I or a pharmaceutically-acceptable salt thereof.

In the above formula, the term "C$_1$–C$_6$ alkyl" represents a straight, cyclic, or branched alkyl chain having from one to six carbon atoms. Typical C$_1$–C$_6$ alkyl groups include methyl, ethyl, n-propyl, isopropyl, n-butyl, isobutyl, sec-butyl, t-butyl, n-pentyl, isopentyl, n-hexyl, cyclopropyl, cyclobutyl, cyclopentyl, cyclohexyl, and the like. The term "C1-C$_4$ alkyl" represents a straight or I0 branched alkyl chain having one to four carbon atoms. Typical C$_1$–C$_4$ alkyl groups include methyl, ethyl, n-propyl, isopropyl, n-butyl, secbutyl, isobutyl, and t-butyl.

The term "Ar" represents groups such as phenyl and substituted phenyl. The term "substituted phenyl", as used herein, represents a phenyl group substituted with one or more moieties chosen from the group consisting of halogen, hydroxy, cyano, nitro, C$_1$–C$_4$ alkyl, C$_1$–C$_4$ alkoxy, acetyl, formyl, trichloromethyl, or trifluoromethyl. Examples of a substituted phenyl group include 4-chlorophenyl, 2,6-dichlorophenyl, 2,5-dichlorophenyl, 3,4-dichlorophenyl,3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2-fluoro- 5-methylphenyl, 2,4,6-trifluorophenyl, 2-trifluoromethylphenyl, 2-chloro-5-trifluoromethylphenyl, 3,5-bis-(trifluoromethyl)phenyl, 2-methoxyphenyl, 3-methoxyphenyl, 3,5-dimethoxyphenyl, 4-hydroxy-3-methylphenyl, 3,5-dimethyl- 4-hydroxyphenyl, 2-methyl-4-nitrophenyl, 4-methoxy-2-nitrophenyl, 2,4-dinitrophenyl, and the like. The term "$C_1$–$C_4$ alkoxy" represents groups such as methoxy, ethoxy, n-propoxy, isopropoxy, n-butoxy, t-butoxy, and the like. The term "halogen" represents fluoro, chloro, bromo, and iodo.

The term "smoking-related bone loss" refers to decreases in bone mineral content, decreases in bone density, increases in bone porosity, and/or decreases in the protein matrix components of bone, which are attributable to smoking.

The term "pharmaceutically-effective amount" is used herein to represent an amount of the formula I compound that is capable of treating smoking-related bone loss. The term "treating" includes inhibiting, preventing, or restraining further bone loss and slowing, stopping progression, or severity of a resultant symptom. The particular dose of the formula I compound will of course be determined by the particular circumstances surrounding the case, including the compound administered, the route of administration, the particular condition treated, and similar considerations.

While all the formula I compounds are useful for treating smoking-related bone loss, certain compounds are preferred. Preferably, $R^1$ and $R^3$ are independently hydrogen, $C_1$–$C_4$ alkyl, —CO—($C_1$–$C_6$ alkyl), or benzyl, and $R^2$ is piperidino or pyrrolidino. Representative compounds from this preferred group include 6-hydroxy-2-(4-hydroxyphenyl)-3-[4-(2-pyrrolidinoethoxy)benzoyl]benzo[b]thiophene, 6-methoxy- 2-(4-methoxyphenyl)-3-[4-(2-piperidinoethoxy)benzoyl]benzo[b]thiophene, 6-acetoxy-2-(4-acetoxyphenyl)-3-[4-(2-pyrrolidinoethoxy)benzoyl]benzo[b]thiophene, and 6-benzyloxy- 2-(4-benzyloxyphenyl)-3-[4-(2-piperidinoethoxy)benzoyl]-benzo[b]thiophene.

More preferably, $R^1$ and $R^3$ are independently hydrogen or $C_1$–$C_4$ alkyl, and $R^2$ is piperidino or pyrrolidino. Representative compounds from this more preferred group include 6-hydroxy-2-(4-hydrophenyl)-3-[4-(2-pyrrolidinoethoxy)benzoyl] benzo[b]thiophene, 6-hydroxy-2-(4-hydroxyphenyl)- 3-[4-(2-piperidinoethoxy)benzoyl]benzo[b]thiophene, 6-methoxy-2-(4-methoxyphenyl)-3-[4-(2-pyrrolidinoethoxy)benzoyl]benzo[b]thiophene, and 6-methoxy-2-(4-methoxyphenyl)- 3-[4-(2-piperidinoethoxy)benzoyl]benzo[b]thiophene. Most preferably, $R^1$ and $R^3$ are hydrogen and $R^2$ is piperidino. This most preferred compound is 6-hydroxy-2-(4-hydroxyphenyl)-3-[4-(2-piperidinoethoxy)benzoyl]benzo[b]thiophene.

The formula I compounds used in the methods of the present invention can be made according to established procedures, such as those described in U.S. Pat. Nos. 4,133,814, 4,418,068, and 4,380,635, all of which are incorporated by reference herein. In general, the process starts with 6-hydroxy-2-(4-hydroxyphenyl)benzo[b]thiophene. This starting compound is protected, acylated at C-3 with a 4-(2-aminoethoxy)benzoyl group, and optionally deprotected to form the formula I compounds. Examples of the preparation of such compounds are provided in the U.S. patents discussed above.

The compounds used in the methods of this invention form pharmaceutically-acceptable acid and, wherein $R^1$ and/or $R^3$ is hydrogen, base addition salts with a wide variety of organic and inorganic acids and bases, including the physiologically-acceptable salts which are often used in pharmaceutical chemistry. Typical inorganic acids used to form such salts include hydrochloric, hydrobromic, hydriodic, nitric, sulfuric, phosphoric, hypophosphoric, and the like. Salts derived from organic acids, such as aliphatic mono- and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically-acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, and β-hydroxybutyrate, butyne-1,4-dioate, hexyne-1,6-dioate, caprate, caprylate, chloride, cinnamate, citrate, formate, fumarate, glycolate, heptanoate, decanoate, hippurate, lactate, malate, maleate, hydroxymaleate, malonate, mandelate, mesylate, nicotinate, isonicotinate, nitrate, oxalate, phthalate, terephthalate, phosphate, monohydroganphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like. The most preferred salt is the hydrochloride salt.

The pharmaceutically-acceptable acid addition salts are typically formed by reacting a compound of formula I with an equimolar or excess amount of acid. The reactants are generally combined in an organic solvent such as methanol, diethyl ether, or benzene. The salt normally precipitates out of solution within about one hour to 10 days and can be isolated by filtration, or the solvent can be stripped off by conventional means.

Bases commonly used for formation of salts include ammonium hydroxide and alkali and alkaline earth metal hydroxides, carbonates, as well as aliphatic primary, secondary, and tertiary amines, and aliphatic diamines. Bases especially useful in the preparation of addition salts include ammonium hydroxide, potassium carbonate, methylamine, diethylamine, ethylenediamine, and cyclohexylamine. These salts are generally prepared by reacting a formula I compound, wherein $R^1$ and/or $R^3$ are hydrogen, with one of the above bases in an organic solvent, such as methanol, diethyl ether, or benzene. The salts are isolated as described in the preceding paragraph.

These pharmaceutically-acceptable salts generally have enhanced solubility characteristics compared to the compound from which they are derived, and thus are often more amenable to formulation as liquids or emulsions.

The formula I compounds are preferably formulated prior to administration such as in a pharmaceutical formulation comprising a compound of formula I and a pharmaceutically-acceptable carrier, diluent, or excipient. These pharmaceutical formulations are prepared by known procedures using well-known and readily available ingredients. In making these compositions, the active ingredient will usually be mixed with a carrier, diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, dermal patches, suppositories, sterile injectible solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cross-linked polyvinylpyrrolidone, cellulose or derivatives thereof, water syrup, methyl cellulose, methyl and propyl hydroxybenzoates, talc, magnesium sterate and mineral oil. The formulations can additionally include lubricating agents, wetting agents (e.g. surfactant), emulsifying and suspending agents, disintegrating agents, preserving agents, sweetening agents, or flavoring agents. Compositions of the inventions may be formulated so as to provide quick, sustained, or delayed release of the active ingredient after administration to the patient by employing procedures well known in the art.

The particular dosage of a compound of formula I required to treat smoking-related bone loss or its symptoms, according to this invention, will depend upon the severity of the condition, the route of administration, and related factors that will be decided by the attending physician. Generally, effective daily doses will be from about 0.1 to about 1000 mg/day, and more typically from about 50 to about 200 mg/day. Such dosages will be administered to a subject in need thereof from once to about three times each day, or more often as needed to effectively treat the condition or symptom.

It is usually preferred to administer a compound of formula I in the form of an acid addition salt, as is customary in the administration of pharmaceuticals bearing a basic group, such as the piperidino group. For such purposes the following oral dosage forms are available.

Formulations

In the formulations which follow, "Active ingredient" means a compound of formula I.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of 20 raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Illustrative compounds that can be used in the methods of the present invention are shown in Table 1.

TABLE 1

| Compound No. | $R^1$ and $R^3$ | $R^2$ | Form |
| --- | --- | --- | --- |
| 1 | —C(O)—(C$_6$H$_4$)—F | piperidino | base |
| 2 | —C(O)—(C$_6$H$_4$)—F | piperidino | HCl |
| 3 | —C(O)—(cyclopropyl) | piperidino | base |
| 4 | —C(O)—(cyclopropyl) | piperidino | HCl |
| 5 | —C(O)CH$_2$CH$_2$CH$_3$ | piperidino | base |
| 6 | —C(O)CH$_2$CH$_2$CH$_3$ | piperidino | HCl |
| 7 | —C(O)C(CH$_3$)$_3$ | piperidino | base |
| 8 | —C(O)C(CH$_3$)$_3$ | piperidino | HCl |
| 9 | —C(O)CH$_2$C(CH$_3$)$_3$ | piperidino | base |
| 10 | —C(O)CH$_2$C(CH$_3$)$_3$ | piperidino | HCl |
| 11 | —C(O)—(C$_6$H$_4$)—CH$_3$ | piperidino | HCl |
| 12 | —C(O)—(C$_6$H$_5$) | piperidino | base |
| 13 | H | piperidino | base |
| 14 | H | piperidino | HCl |
| 15 | H | pyrrolodino | base |
| 16 | H | pyrrolodino | HCl |
| 17 | H | hexamethylene-imino | HCl |
| 18 | CH$_3$ | piperidino | HCl |

The utility of the compounds of formula I is illustrated by the positive impact they have in at least one of the assays described below.

EXAMPLE 1

A model of post-menopausal osteoporosis was used in which effects of different treatments upon femur density were determined. Seventy-five day old female Sprague Dawley rats (weight range of 225 g to 275 g) were obtained from Charles River Laboratories (Portage, Mich.). They were housed in groups of 3 and had ad libitum access to food (calcium content approximately 1%) and water. Room temperature was maintained at 22.2°±1.7° C. with a minimum relative humidity of 40%. The photoperiod in the room was 12 hours light and 12 hours dark.

One week after arrival, the rats underwent bilateral ovariectomy under anesthesia [44 mg/kg Ketamine and mg/kg Xylazine (Butler, Indianapolis, Ind.) administered intramuscularly]. Treatment with vehicle, estrogen, or a compound of formula I was initiated on the day of surgery following recovery from anesthesia. Oral dosage was by gavage in 0.5 mL of 1% carboxymethylcellulose (CMC). Body weight was determined at the time of surgery and weekly thereafter and the dosage was adjusted with changes in body weight. Vehicle or estrogen treated ovariectomized (ovex) rats and non-ovariectomized (intact) rats were evaluated in parallel with each experimental group to serve as negative and positive controls.

The rats were treated daily for 35 days (6 rats per treatment group) and sacrificed by decapitation on the 36th day. The 35 day time period was sufficient to allow maximal reduction in bone density, measured as described herein. The right femurs were excised and scanned at the distal metaphysis 1 mm from the patellar groove with single photon absorptiometry. Results of the densitometer measurements represent a calculation of bone density as a function of the bone mineral content and bone width.

The results of control treatments from five separate experiments are accumulated in Table 2. In summary, ovariectomy of the rats caused a reduction in femur density of about 25% as compared to intact vehicle treated controls. Estrogen, administered in the orally active form of ethynyl estradiol (EE$_2$), prevented this loss of bone in a dose dependent manner. Results are reported as the mean of measurements from thirty rats ± the standard error of the mean.

In these studies, raloxifene also prevented bone loss in a dose dependent manner. The results of five assays using raloxifene are combined in Table 3. Accordingly, each point reflects the responses of thirty rats and depicts a typical dose response curve for raloxifene in this model. Results are reported as the mean ± the standard error of the mean.

TABLE 2

| | Bone Density (mg/cm/cm) |
| --- | --- |
| Ovariectomy control (0.5 mL CMC oral) | 170 ± 3 |
| Intact control (0.5 mL CMC oral) | 220 ± 4 |
| EE$_2$ 100 µg/kg, oral | 210 ± 4 |

TABLE 3

| | Bone Density (mg/cm/cm) |
|---|---|
| Ovariectomy control (0.5 mL CMC oral) | 171 ± 3 |
| Intact control (0.5 mL CMC oral) | 222 ± 3 |
| raloxifene 0.01 mg/kg, oral | 176 ± 3 |
| raloxifene 0.10 mg/kg, oral | 197 ± 3 |
| raloxifene 1.00 mg/kg, oral | 201 ± 3 |
| raloxifene 10.00 mg/kg, oral | 199 ± 3 |

EXAMPLE 2

Other compounds of formula I were administered orally in the rat assay described in Example 1. Table 4 reports the effect of a 1 mg/kg dose of each compound in terms of a percent inhibition of bone loss.

TABLE 4

| Compound Number | % Inhibition of Bone Loss[a] |
|---|---|
| 2 | 86 |
| 6 | 24 |
| 8 | 66 |
| 10 | 52 |
| 11 | 26 |
| 12 | 60 |
| 16 | 25 |
| 18 | 26 |

[a]Percent inhibition of bone loss = (bone density of treated ovex animals - bone density of untreated ovex animals) ÷ (bone density of estrogen treated ovex animals - bone density of untreated ovex animals) × 100.

I claim:

1. A method for treating smoking-related bone loss comprising administering to a human in need thereof a pharmaceutically-effective amount of a compound having the formula

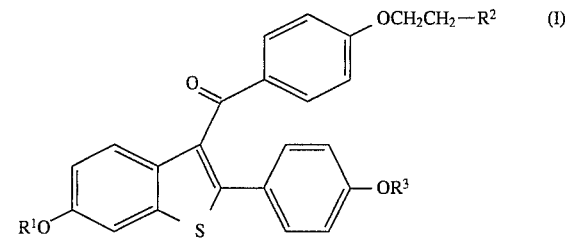

wherein

R$^1$ and R$^3$ are independently hydrogen, C$_1$–C$_4$ alkyl, —CO—(C$_1$–C$_6$ alkyl), or —CH$_2$Ar, —CO—Ar, wherein Ar is phenyl or substituted phenyl;

R$^2$ is selected from the group consisting of pyrrolidino, hexamethyleneimino, and piperidino; or a pharmaceutically-acceptable salt thereof.

2. The method of claim 1 wherein R$^1$ and R$^3$ are independently hydrogen, C$_1$–C$_4$ alkyl, —CO—(C$_1$–C$_6$ alkyl), or benzyl; and R$^2$ is piperidino or pyrrolidino.

3. The method of claim 2 wherein R$^1$ and R$^3$ are independently hydrogen or C$_1$–C$_4$ alkyl, and R$^2$ is piperidino or pyrrolidino.

4. The method of claim 3 wherein R$^1$ and R$^3$ are hydrogen and R$^2$ is piperidino or pyrrolidino.

5. The method of claim 4 wherein R$^2$ is piperidino.

6. The method of claim 5 wherein said pharmaceutically-acceptable salt is the hydrochloride salt.

* * * * *